United States Patent

Ohta et al.

[11] Patent Number: 6,063,635
[45] Date of Patent: May 16, 2000

[54] DISPENSING METHOD FOR AUTOMATIC SAMPLE ANALYSIS SYSTEMS

[75] Inventors: Yumi Ohta, Funabashi; Tetsuya Morikawa, Matsudo; Tetsuya Shiga, Higashikatsushika-gun; Yuko Ishii; Mitsuhiro Saito, both of Kashiwa, all of Japan

[73] Assignee: Abbott Laboratories, Abbott Park, Ill.

[21] Appl. No.: 09/147,863

[22] PCT Filed: Sep. 2, 1997

[86] PCT No.: PCT/JP97/03065

§ 371 Date: Mar. 17, 1999

§ 102(e) Date: Mar. 17, 1999

[87] PCT Pub. No.: WO98/14785

PCT Pub. Date: Sep. 4, 1998

[51] Int. Cl.[7] .................................................. G01N 35/10
[52] U.S. Cl. .............................. 436/54; 436/49; 436/50; 436/179; 436/180; 422/67; 422/100
[58] Field of Search .................................. 436/43, 49, 50, 436/54, 174, 179, 180; 422/63, 67, 81, 100, 105; 73/864.01, 864.11

[56] References Cited

U.S. PATENT DOCUMENTS

| | | |
|---|---|---|
| 4,794,085 | 12/1988 | Jessop et al. . |
| 5,078,970 | 1/1992 | Teodorescu et al. .................... 422/100 |
| 5,236,473 | 8/1993 | Kraus et al. ................................ 95/30 |
| 5,463,895 | 11/1995 | Brentz . |
| 5,555,767 | 9/1996 | Makino et al. ............................ 73/863 |
| 5,612,227 | 3/1997 | Inoue et al. .............................. 436/180 |

FOREIGN PATENT DOCUMENTS

| | | | |
|---|---|---|---|
| 0526210 | 2/1993 | European Pat. Off. | G01N 35/06 |
| 0629859 | 9/1993 | European Pat. Off. | G01N 35/06 |
| 4359154 | 12/1992 | Japan | G01N 35/06 |
| 6210160 | 8/1994 | Japan | B01J 19/10 |
| 7239334 | 9/1995 | Japan | G01N 35/10 |
| 7301586 | 11/1995 | Japan | G01N 1/36 |
| 9208545 | 5/1992 | WIPO | B01L 3/02 |

OTHER PUBLICATIONS

European Search Report from EP 97 93 7874.
I. Koji, Patent Abstracts of Japan, vol. 012, No. 226, Jun. 28, 1988.
International Search Report from PCT/JP97/03065.

*Primary Examiner*—Long V. Le
*Attorney, Agent, or Firm*—Mark C. Bach

[57] ABSTRACT

A diluent is discharged by a dispensing device into a dilution bath 11 containing a sample, and a given amount of a diluted sample 12 is sucked from the upper face by the dispensing device and discarded by discharging it into a waste fluid cup to remove many small bubbles 13 generated during the preparation of the diluted sample used for determination. The diluted sample 12 remaining in the dilution bath 11 is used for determination to improve the precision and reproducibility of determination and to prevent failure of the dispensing device due to inclusion of bubbles.

2 Claims, 4 Drawing Sheets

DISPENSING METHOD FOR AUTOMATIC SAMPLE ANALYSIS SYSTEMS

FIELD OF THE INVENTION

The present invention relates to a dispensing method for automatic sample analysis systems, particularly a method for removing bubbles generated when a sample is diluted in automatic sample analysis systems, fully automatic analysis systems or the like performing multiple random determinations.

PRIOR ART

In order to improve performance of random-access multiple sample analysis systems automatically operating from the sample dispensing step to the determination step, there has recently been an increasing need for random access to even test items that should be determined after the sample or reagent has been diluted.

The sample or reagent is diluted typically by discharging a diluent from a nozzle into a dilution vessel at a suitable speed to omit stirring action and shorten the time for discharging by simultaneous mixing and discharging, with the result that many small bubbles may be generated in upper layers of the diluted sample.

In systems for sequentially and automatically determining a single item on a plurality of samples, the plurality of samples are sequentially diluted and then successively mixed with a reagent for determination so that many bubbles generated during dilution decrease or disappear after the lapse of a given period. Residual bubbles are impelled toward the wall of the vessel by inertia force or centrifugal force without causing significant problems during dispensing, because the samples are typically moved on a carousel.

However, bubbles generated in automatic sample analysis systems for randomly performing various types of multiple determinations tend to remain because samples are not moved during a short interval from dilution to determination for the reason that it is more efficient to mix a sample with a reagent for determination immediately after the sample is diluted without moving the vessel.

In addition, automatic sample analysis systems for performing multiple random determinations are less likely to form a bubble-free liquid surface at the center of the dilution vessel, because each vessel is designed to be small for the purpose of diminishing the overall system size and mixing requires some discharge speed.

Bubbles generated during dilution enter the pipette to impair dispensing precision when the diluted fluid is dispensed, which results in deterioration of the precision and reproducibility of test results.

Various apparatus for forcedly removing bubbles from the channel have been proposed, e.g. an apparatus having an upper bubble reservoir, an apparatus for pumping away bubbles detected by a sensor provided in the channel, an apparatus having a dispensing nozzle with one of the branched ends connected to a discharge channel an apparatus having an upper constricted zone to remove bubbles under reduced pressure, etc.

Such apparatus for removing bubbles from the channel add a sensor or pipeline to automatic sample analysis systems already having a complex structure with many movable parts, which further complicates the structure of the entire system to hinder handling and prolong the cycle time for determination.

Other apparatus than those for forcedly removing bubbles have also been proposed, e.g. an apparatus for dispensing samples after detecting bubble sites in the channel to confirm the absence of bubbles, an apparatus for retrying suction once bubbles have entered during suction, an apparatus for acting to expel the air at the end of the dispensing tube before dispensing, an apparatus for correctly detecting the liquid level during suction even when bubbles exist.

However, automatic sample analysis systems with these apparatus also require a special sensor or operation to hinder handling and prolong the cycle time.

In order to overcome the above problems, an object of the present invention is to provide a dispensing method for automatic sample analysis systems, which can dispense samples from which have been removed bubbles generated during dilution without adding any special structure or time-consuming operation.

SUMMARY OF THE INVENTION

The above object can be achieved by the dispensing method according to the present invention for automatic sample analysis systems performing multiple random determinations, comprising: sucking and discharging a predetermined amount of a diluent by a dispensing means into a vessel containing a sample, mixing said sample with said diluent to prepare a diluted sample, then sucking a given amount of said diluted sample by said dispensing means from upper layers of said diluted sample to remove bubbles generated during dilution existing at the upper layers of said diluted sample from said vessel before a part of said diluted sample is sucked by said dispensing means to discharge it into a reaction bath for determination, and discharging said given amount of said diluted sample to discard it.

In the dispensing method of the present invention, the given amount of said diluted sample to be sucked from upper layers of said diluted sample may be predetermined according to the nature of the sample or the type of determination.

In the dispensing method of the present invention, said dispensing operation may be temporarily stopped when any bubble generated during dilution is detected to be greater than a given size.

BRIEF DESCRIPTION OF THE DRAWINGS

An embodiment of the present invention will now be explained in detail with reference to the attached drawings, in which.

Numeral references represent the following elements: 1: cabinet; 2: boom assembly; 2a: probe; 3: carousel; 4: waste fluid cup; 5: washing cup; 6: sample cup; 7: reagent pack; 8: reaction cell; 11: dilution bath; 12: diluted sample; 13: bubble.

DETAILED DESCRIPTION OF THE INVENTION

Figure 1:
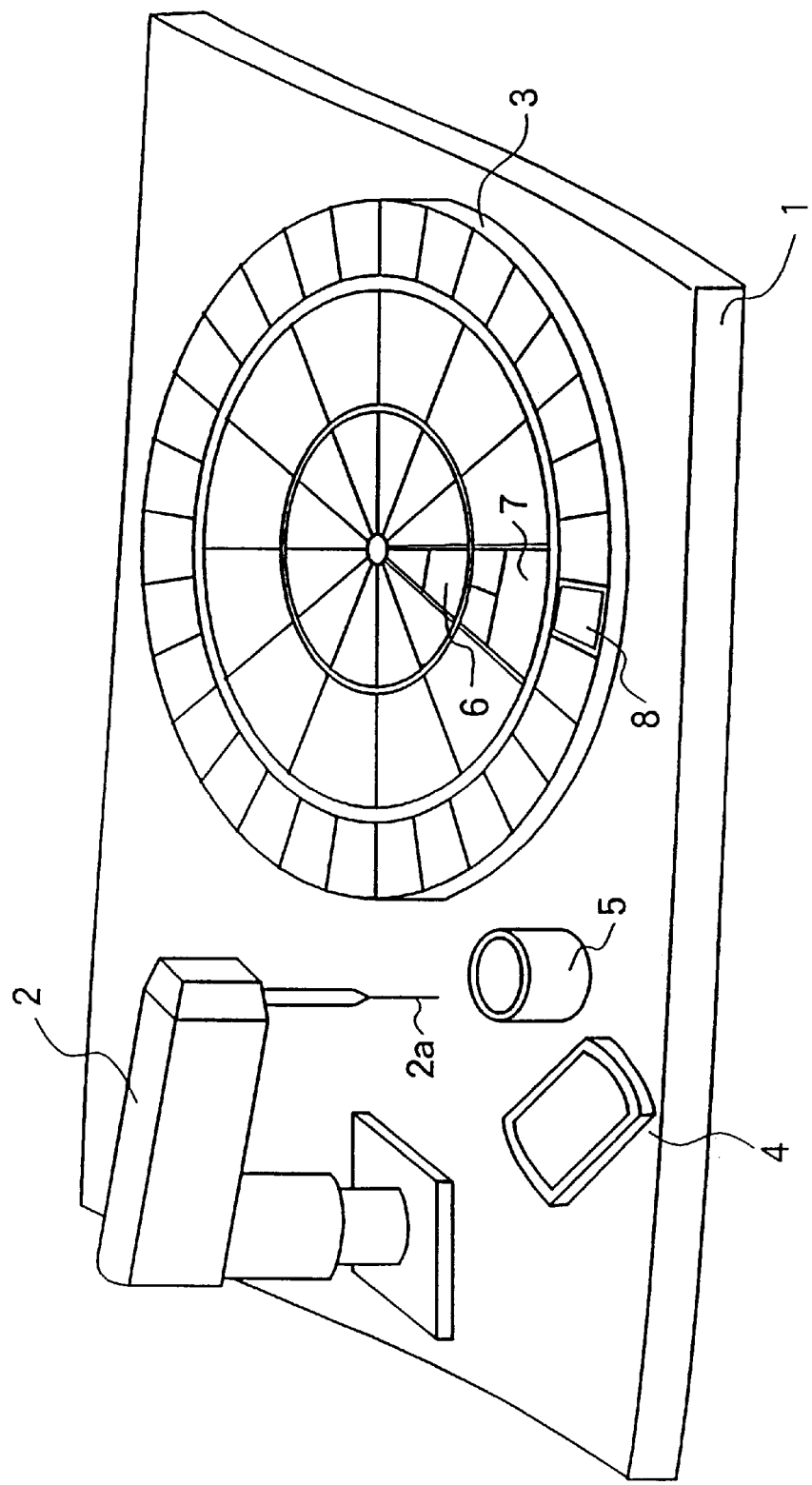
FIG. 1 is a schematic view showing the structure of an automatic sample analysis system for carrying out the dispensing method of the present invention.

FIG. 1 is a schematic view showing the structure of an automatic sample analysis system performing multiple random determinations for carrying out the dispensing method of the present invention.

The present sample analysis system comprises, on a cabinet 1, a boom assembly 2 serving as a dispensing means, a carousel 3 rotated according to the assay selected, a waste fluid cup 4 for discarding waste fluid and a washing cup 5 for washing a probe.

The boom assembly 2 has a pipetting arm forming a movable part, a tapered probe 2a fitted at an end of the pipetting arm and a syringe pump connected to the probe 2a via a tube, and is designed to accomplish a dispensing operation by moving the pipetting arm to accurately suck and discharge minor amounts of fluid from the probe via the syringe pump.

The carousel 3 has three concentric parts, each equiangularly divided into compartments each capable of receiving therein a part 6 for receiving a rack with a sample cup containing a sample, a reagent pack 7 containing a reagent necessary for determination, and a reaction cell 8 including a plurality of reaction baths for diluting the dispensed sample and reacting the dispensed sample with a reagent.

Now, the operation of said automatic sample analysis system is explained with reference to the flow chart of FIG. 2.

Initially, test requirements are checked, e.g. whether or not the reaction cell 8 has been mounted on the carousel 3 by the user, whether or not a sample, diluent, reagent or the like necessary for determination have been prepared, what is the schedule of determination. (S1).

If the result (S2) shows that all the test requirements are satisfied, the carousel is rotated to a given starting position (S3).

If the result (S2) shows that all the test requirements are not satisfied, resetting is demanded and the user makes resetting according to the demand (S8).

The sample in the sample cup is dispensed into a reaction bath of the reaction cell by the dispensing means (S4).

The reagent in the reagent pack is dispensed into the reaction bath containing the sample by the dispensing means and mixed with the sample (S5).

The carousel is rotated to incubate the sample with the reagent for a given period in the reaction bath to perform determination/assay by determination/assay means not shown (S6). If a carousel for determination/assay is separately provided, the reaction cell is transferred by a transferring mechanism for determination/assay.

Whether or not all the selected determinations/assays have been completed is checked (S7). If all the determinations/assays have been completed, a given operation is done to complete the process. If any determination/assay has not been completed, the carousel is rotated to repeat the process of S3 to S7 for the next determination/assay.

Figure 2:
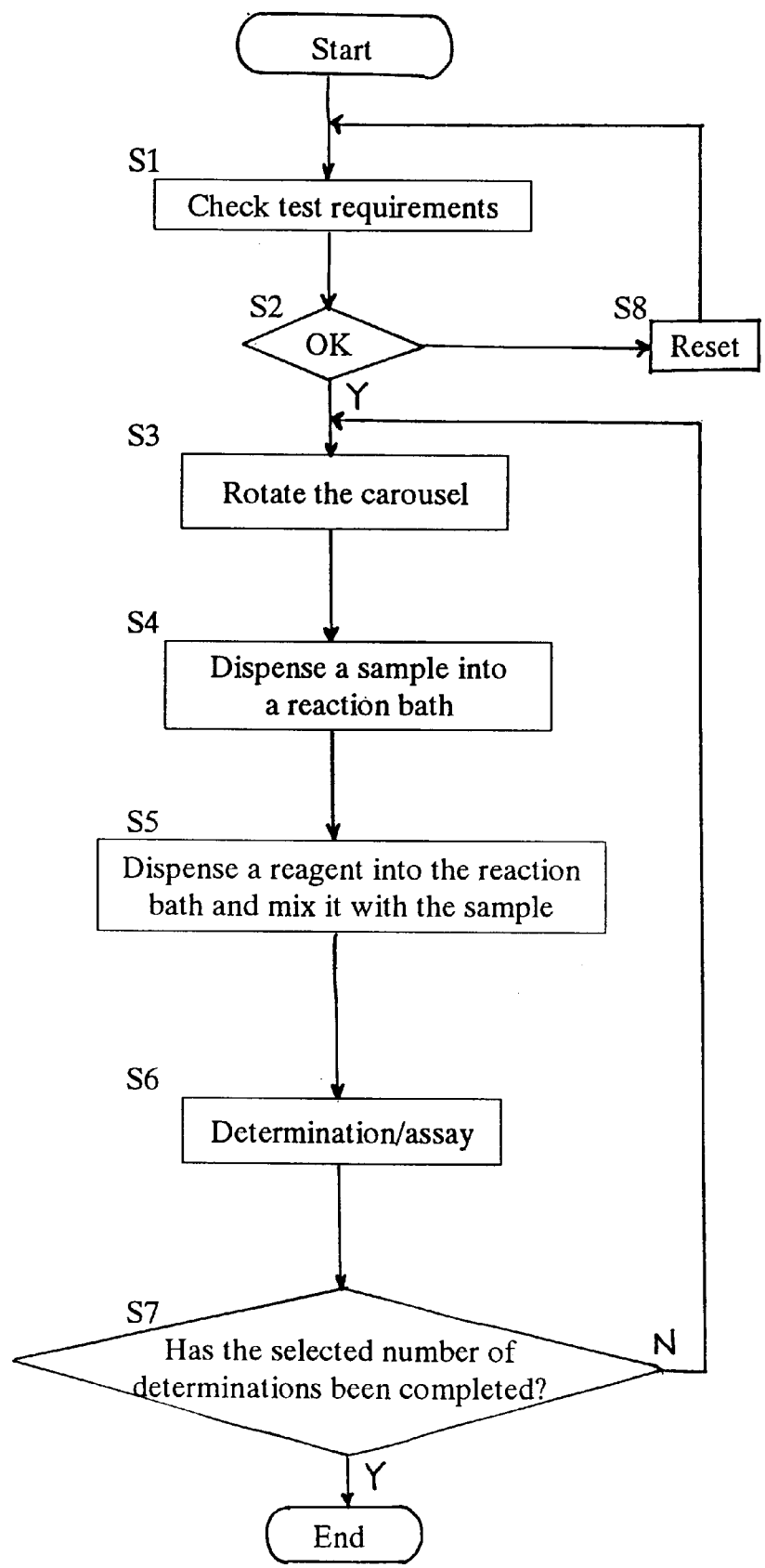
FIG. 2 is a flow chart showing the determination operation of the system shown in FIG. 1.
Figure 3:
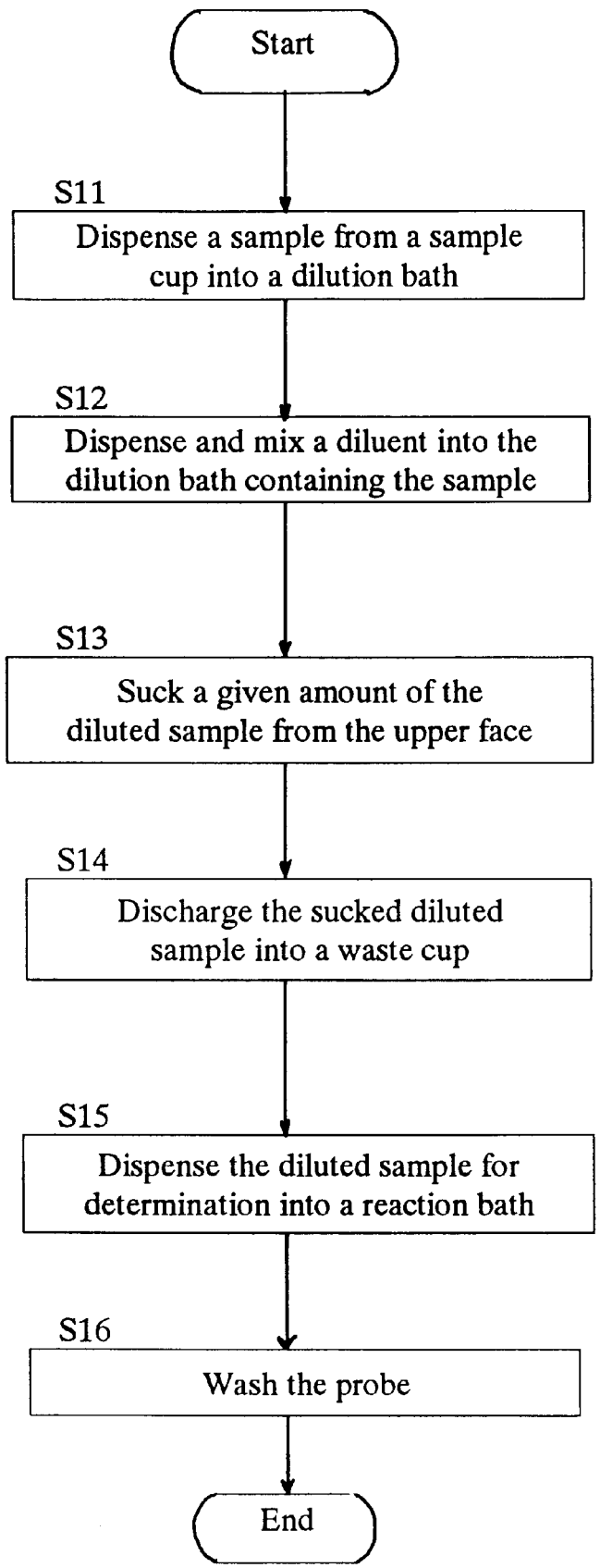
FIG. 3 is a flow chart showing the dispensing operation according to the present invention.
Figure 4:
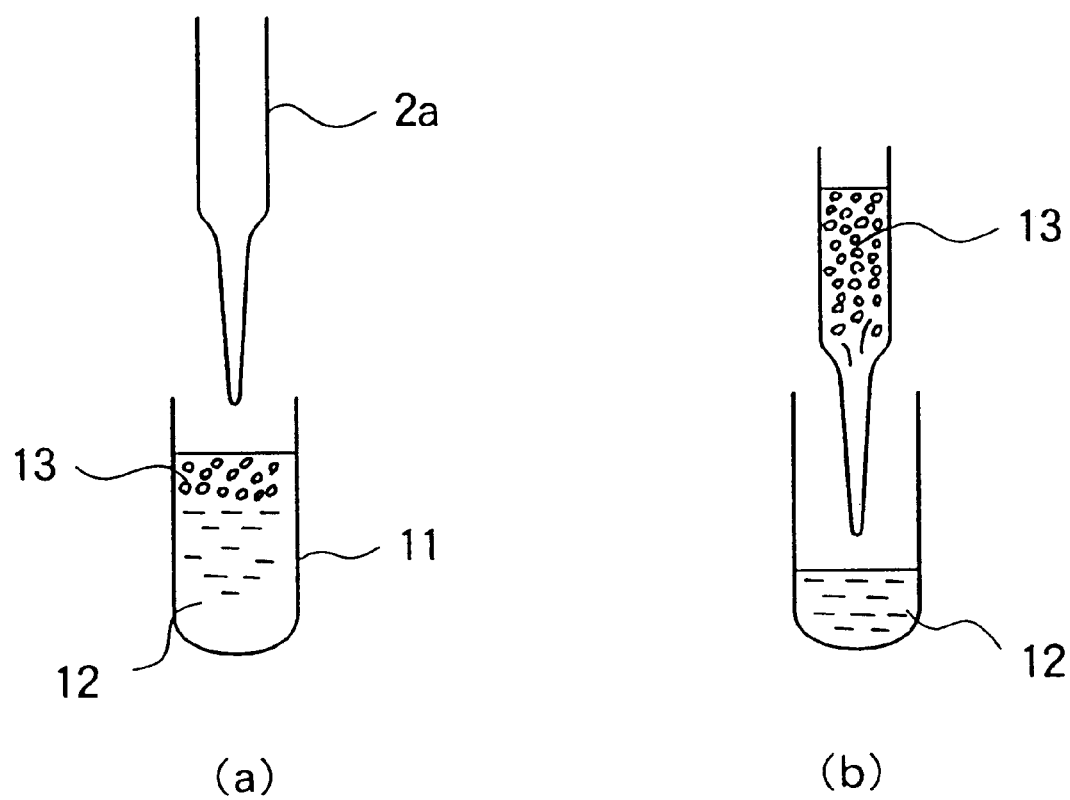
FIG. 4(a) and 4(b) illustrates the dispensing method according to the present invention.

Then, the dispensing operation performed at S4 in the flow chart of FIG. 2 is explained in detail with reference to the flow chart of FIG. 3 and FIG. 4.

The probe is moved onto the sample cup containing the sample to suck a given amount of the sample, and the probe is moved onto the dilution bath of the reaction cell 8 to discharge the sucked sample (S11).

The diluent is sucked from the reagent pack 7, and the probe is moved onto the dilution bath to discharge the sucked diluent into the dilution bath containing the sample at a suitable speed to mix the diluent with the sample (S12). During then, many bubbles are generated in upper layers in the dilution bath as the diluent is discharged, as shown in FIG. 4(a).

FIG. 4(a) shows the state after the diluent has been discharged into the dilution bath 11 and used for dilution there, in which the references 2a, 12 and 13 represent the probe, diluted sample and bubbles generated in upper layers of the diluted sample, respectively.

In the same position, a given amount of the diluted sample in the dilution bath is then sucked from the upper layers by the probe to remove the bubbles generated, as shown in FIG. 4(b) (S13).

The amount of fluid sucked depends on not only the amount of the sample and diluent used but also the nature of the sample as well as the nature of the diluent used and dilution degree, so that it is determined for each determination or each nature of the sample. The probe is moved onto the waste liquid cup to discharge the sucked fluid containing bubbles into the waste fluid cup to discard it (S14).

The probe is moved again onto the dilution bath to suck the amount for determination from the dilution bath containing the diluted sample, and the probe is moved to discharge the sucked fluid into the reaction bath (S15).

Before dispensing the reagent, the probe carrying the sample is moved into the washing cup to wash it (S16).

Among the dispensing operation steps described above, S13 and S14 are unique to the dispensing method of the present invention while the other steps are the same as conventionally used in automatic sample analysis systems.

The operation in the step S13 takes place immediately after the diluent is discharged onto the dilution bath containing the dispensed sample as described above, which causes no time loss due to movement of the dispensing means. The operation at S14 requires movement of the dispensing means to the waste fluid cup, but the time for this movement is relatively slighter than the time for the washing operation at S16 and thus causes no special problem in terms of the total determination period.

The dispensing means may be provided with a liquid level sensor or the like to temporarily stop the dispensing operation when it detects any bubble greater than a given size, which is difficult to suck with the diluted sample or contacts the probe to contaminate it.

When the dispensing operation is temporarily stopped, the next operation may involve diluting again the sample of interest or jumping to determination of the next sample or the like.

EXAMPLE

The following example relates to the determination precision obtained by applying the dispensing method of the present invention as compared with a conventional dispensing method.

An automatic sample analysis system performing multiple random determinations was used to determine $\beta_2$-microglobulin (B2-M) by the double antibody sandwich method, as follows.

From a sample cup was sucked 50 µl of a B2-M sample and the sucked sample was discharged into a dilution bath of a reaction cell.

From a reagent pack was sucked 200 µl of a buffer and discharged into the dilution bath containing the sample, where the sample was diluted 5-fold to prepare a sample dilution.

In order to remove bubbles generated by dilution, 100 µl were sucked from the upper face of the sample dilution and discharged into a waste fluid cup and thus discarded.

For determination, 10 µl of the sample dilution remaining in the dilution bath of the reaction cell was sucked and discharged into a reaction bath of the reaction cell.

From the reagent pack were sucked anti-B2-M antibody-immobilized particles and discharged into the reaction bath of the reaction cell, where they were mixed with the sample dilution to carry out the first reaction.

After the lapse of a given reaction period, the mixed solution was placed on a membrane and the particles were washed with a buffer, then an alkaline phosphatase-labeled anti-B2-M antibody solution was dispensed to carry out the second reaction.

Finally, the particles were washed again, and then an MUP (methylumbelliferyl phosphate) substrate solution was added to determine the B2-M value in the sample calculated from the increase rate of fluorescence intensity with time.

According to a conventional dispensing method for comparison, the B2-M value in the sample was determined by the same procedure except that 100 $\mu$l was not sucked and discarded from the upper layers of the sample dilution.

The same sample was subjected to 6×10 runs and 6×6 runs of the above determination respectively in two similar systems (system A and system B).

The determination precision obtained by applying the dispensing method of the present invention was 2.8% (system A) and 2.0% (system B) expressed as average of coefficient of variation in one run, with the overall coefficient of variation in the total runs being 3.3% (system A) and 3.1% (system B).

The determination precision obtained by applying the conventional dispensing method for comparison was 5.3% (system A) and 5.5% (system B) expressed as average of coefficient of variation in one run, with the overall coefficient of variation in the total runs being 5.4% (system A) and 6.4% (system B).

ADVANTAGES OF THE INVENTION

The dispensing method of the present invention can effectively remove bubbles generated when a sample is diluted in automatic sample analysis systems performing multiple random determinations. Thus, it can improve the precision and reproducibility of determination and prevent failure of dispensing means due to inclusion of bubbles, without adding any special structure or time-consuming operation.

According to an embodiment of the present invention, the given amount sucked from the diluted sample may be predetermined depending on the nature of the sample or the type of determination, whereby bubbles can be effectively removed before determination according to the bubbling degree for each nature of the sample or each test item.

According to an embodiment of the present invention, the dispensing operation may be temporarily stopped when any bubble generated during dilution is detected to be greater than a given size, whereby extensive contamination of the probe or failure of the dispensing means due to large bubbles can be prevented.

What is claimed is:

1. A dispensing method for automatic sample analysis systems performing multiple random access analysis, comprising the steps of:

sucking a given amount of a diluent by a dispensing means, discharging said diluent into a vessel containing a sample therein, and mixing said sample with said diluent to prepare a diluted sample;

sucking a given amount of said diluted sample by said dispensing means from upper layers of said diluted sample to remove bubbles in the upper layers generated during dilution before a given amount of said diluted sample is sucked by said dispensing means to discharge it into a reaction bath for analysis; and discarding said given amount of said diluted sample as waste, wherein the amount of said diluted sample to be sucked from said upper layers of said diluted sample is predetermined depending on the nature of the sample of the type of assay.

2. A dispensing method according to claim 1 wherein said dispensing operation is temporarily stopped when the size of any bubble generated during dilution is detected to be greater than a given size.

* * * * *

UNITED STATES PATENT AND TRADEMARK OFFICE
CERTIFICATE OF CORRECTION

PATENT NO. : 6,063,635
DATED : May 16, 2000
INVENTOR(S) : Yumi Ohta et al.

It is certified that error appears in the above-identified patent and that said Letters Patent is hereby corrected as shown below:

Col. 6, line 33
 replace "sample of"
 with --sample or--.

Signed and Sealed this

Twenty-ninth Day of May, 2001

Attest:

NICHOLAS P. GODICI

*Attesting Officer*    *Acting Director of the United States Patent and Trademark Office*